United States Patent [19]

Nash

[11] 4,260,380
[45] Apr. 7, 1981

[54] VIBRATORY DEVICE WITH FLUID TRANSPORT MEANS

[75] Inventor: John E. Nash, Downingtown, Pa.

[73] Assignee: Syntex (U.S.A.) Inc., Palo Alto, Calif.

[21] Appl. No.: 26,378

[22] Filed: Apr. 2, 1979

[51] Int. Cl.³ ............................................. A61C 3/03
[52] U.S. Cl. ................................. 433/119; 433/120; 433/132
[58] Field of Search ............... 433/86, 118, 119, 120, 433/122, 132; 310/26, 50

[56] References Cited

U.S. PATENT DOCUMENTS

| | | | |
|---|---|---|---|
| Re. 29,687 | 7/1978 | Sertich | 433/120 |
| 3,444,622 | 5/1969 | Mills et al. | 433/120 X |
| 3,589,012 | 6/1971 | Richman | 433/86 |
| 3,930,173 | 12/1975 | Banko | 310/26 |
| 4,038,571 | 7/1977 | Hellenkamp | 310/323 X |

Primary Examiner—William A. Cuchlinski, Jr.
Attorney, Agent, or Firm—John A. Dhuey

[57] ABSTRACT

An air-driven dental scaler is disclosed having water transport means for delivering water to a scaling type work tool. The water transport means comprises a tube coaxially disposed within a vibratable hollow shaft. The water tube is supported at one end within a resilient support assembly which provides a water seal between the coaxially disposed vibratable shaft and water transport tube. The water seal assembly is positioned forwardly of a vibrational node characteristic of a standing wave created during operation of the dental scaler. An axial force exerted on the water seal assembly during vibration of the vibratable shaft improves the efficacy of the water seal between the shaft and the water transport tube. The single, resilient support for the water transport tube provides for quick replacement of the water tube in the event of clogging of the tube by mineral deposits or sediment.

The invention is also applicable to air- or fluid-driven vibratory devices having non-driving fluid transport means associated therewith.

28 Claims, 7 Drawing Figures

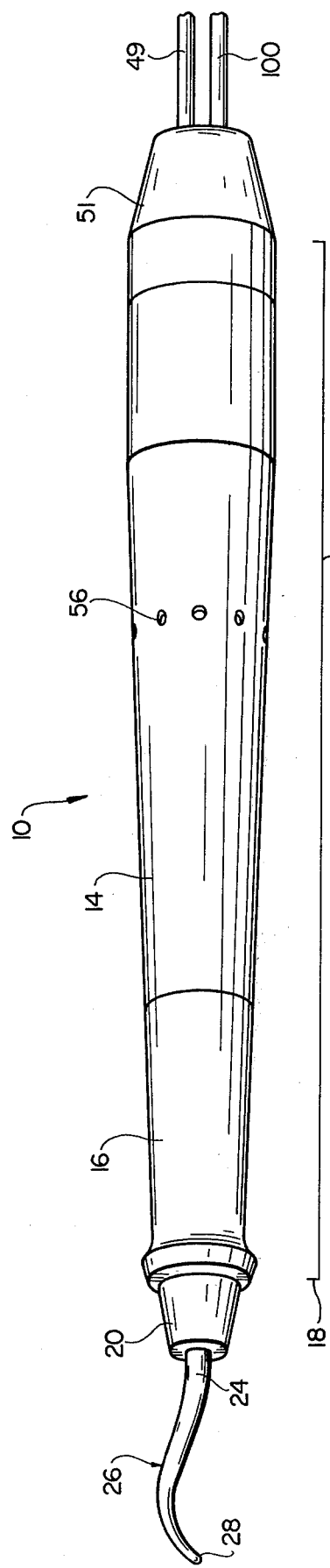
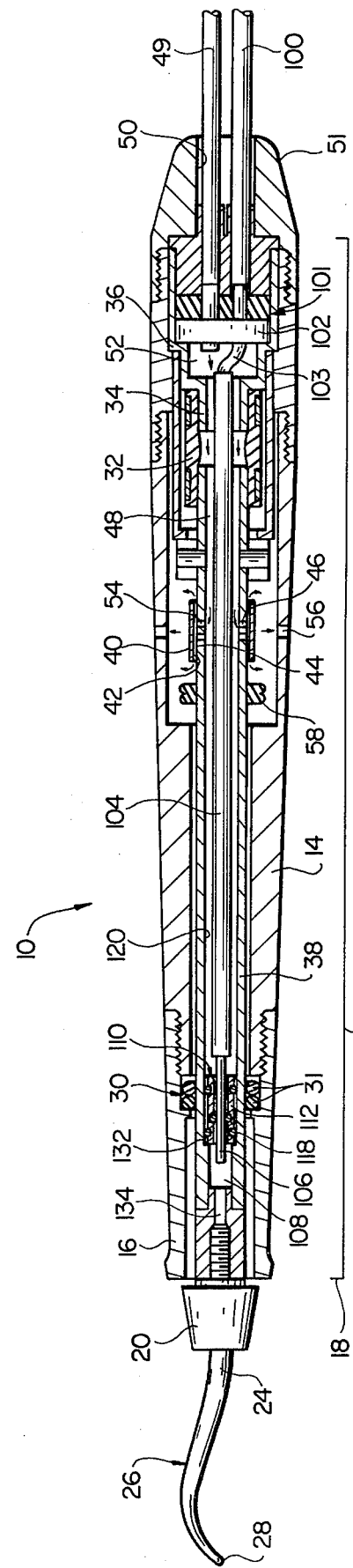

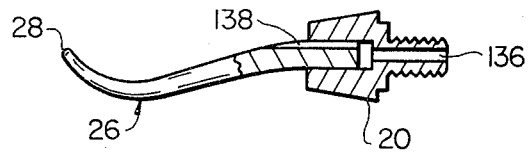
FIG_7
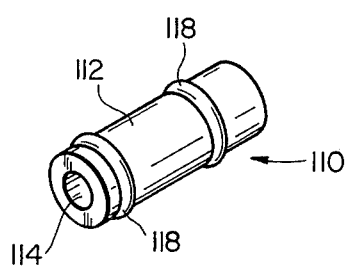
FIG_3
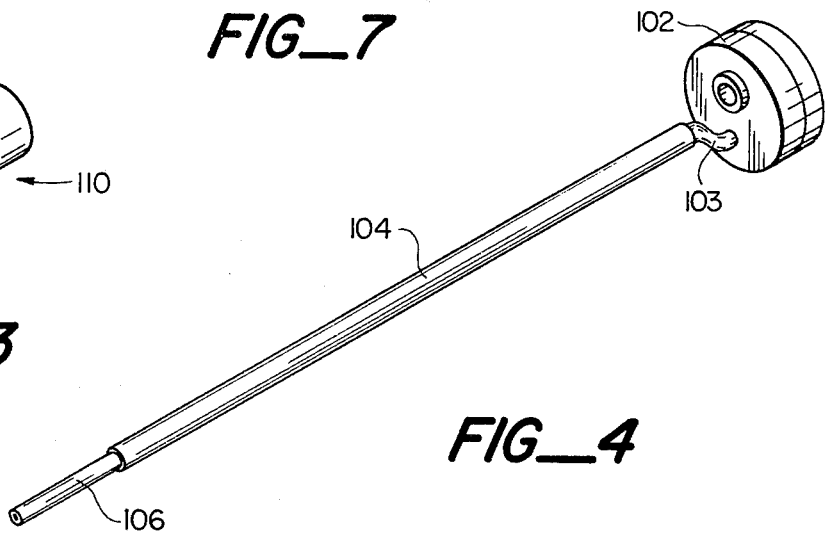
FIG_4
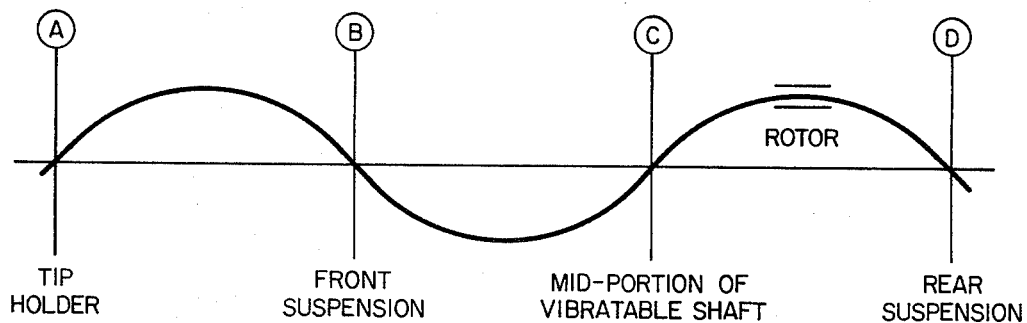
FIG_5
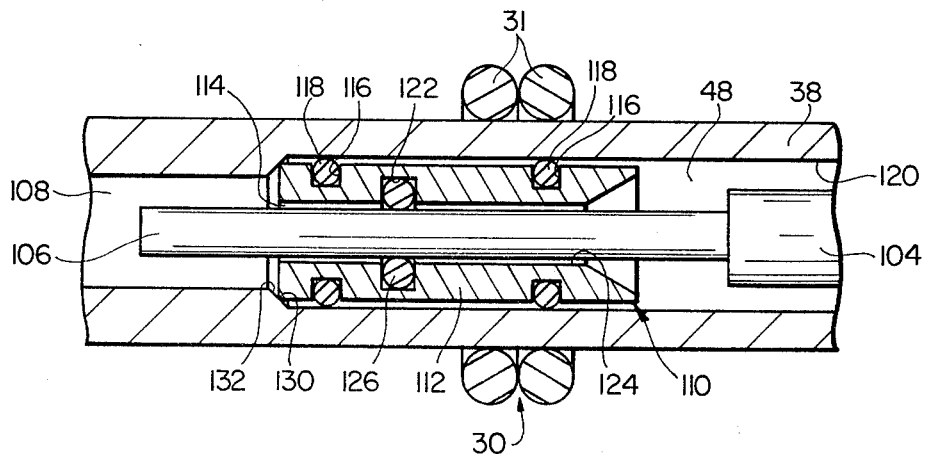
FIG_6

VIBRATORY DEVICE WITH FLUID TRANSPORT MEANS

BACKGROUND OF THE INVENTION

1. Field

Power driven dental scalers are well known. Of particular interest herein is a dental scaler having vibratable scaling work tool for removing calculus from teeth, which dental scaler utilizes a stream of water to aid in scaling efficiency and in removal of accumulated debris.

2. State of the Art

Of the power driven dental scalers currently available, most common are scalers utilizing a flow of compressed air or a solid-state ultrasonic transducer to cause a scraping type work tool to vibrate.

Typical of the earlier air-driven dental scalers are those of U.S. Pat. No. 3,082,529 and No. 3,444,622 to Mills et al, which scalers utilize an air-driven ball contained in a chmaber. Movement of the ball against the walls of the chamber imparts vibration to the chamber, which vibrations are then transmitted to the scraping tool. A more recent type of air-driven scaler, described in U.S. Pat. No. 3,526,962 to Fuerst, utilizes a rotatable mandrel which has an irregularly-shaped tip engaged with a reciprocable block in which the mandrel tip is received.

It is characteristically a problem of these air driven scalers that much of the vibrational energy generated by the vibrator motor is transferred to the handle portion of the dental scaler rather than to the scraper work tool. Moreover, the modes of vibration of these scalers may change as moving parts of the vibration generating mechanism wear with time.

In U.S. Pat. No. 3,703,037 to Robinson, there is described a dental scaler which utilizes a solid state ultrasonic transducer to provide constant modes of vibration for coupling with particular types of work tools. One disadvantage of the ultrasonic scaler, however, is the cost of the transducer and its fairly sophisticated ultrasonic generator.

A different air-driven dental scaler is disclosed in U.S. Pat. No. Re. 29,687 to Sertich. This dental scaler has very few moving parts as compared to the aforementioned mechanically complicated air-driven scalers and provides efficient transfer of vibrational energy to a scraping-type work tool with relatively little vibration being transferred to the handle portion of the instrument. Moreover, this type of scaler provides uniform modes of constant vibration which may be matched with the vibratory modes of various types of work tools without the need for complicated electronic components.

It has been found that a flow of water over a tooth surface can provide increased scaling efficiency and patient comfort by lubricating the tooth surface and by flushing scaled debris and blood from the surface and area being cleaned. A solid state type dental scaler utilizing a flow of water to improve cleaning efficiency is described in U.S. Pat. No. 4,038,571 to Hellenkamp. One disadvantage of the Hellenkamp device, in addition to that of relatively high cost, is the shock hazard associated with the use of both electrical power and water in a hand-held instrument.

It would be desirable to have a non-electrical, air-driven dental scaler having means for delivering water to the scaler tip. Of particular advantage would be a relatively low-cost air-driven dental scaler having the scaling efficiency advantages of the "Sertich-type" scaler together with the advantage of water flow at the scaler tip to enhance the cleaning action.

A particular problem which occurs frequently in the use of dental instruments utilizing water transport tubes with small bores (such as 0.020 inch or less) is clogging of the tube with sediment or minerals carried in the stream of water. Hence, it would be of benefit for a scaler to have a water supply tube that is easily accessible and quickly replaceable in the event it becomes clogged.

There is need, therefore, for a compact, readily repairable air-driven dental scaler having means incorporated therein for delivering water to a scaling tip.

SUMMARY OF THE INVENTION

An air-driven vibratory-type dental scaler is provided which comprises elongated casing means having a proximal or rearward end and a distal or forward end, resilient support means within the casing means, a substantially rigid hollow shaft supported within the elongated casing means by the resilient support means, work tool connecting means attached to the distal end of the hollow shaft, the work tool connecting means capable of operatively connecting a work tool to the distal end of the hollow shaft, means for imparting vibration to the resiliently supported hollow shaft when the dental scaler is energized to provide vibratory movement to a work tool connected to the work tool connecting means, water transport means comprising a tube disposed substantially coaxially within the hollow shaft, the tube having a proximal end and a distal end, a water seal assembly for supporting the distal end of the water transport tube within the hollow shaft, the dental scaler having a vibrational node near the distal end of the hollow shaft, the water seal assembly disposed forwardly of the vibrational node at a distance up to about one-quarter of a vibrational wavelength, preferably about one-sixteenth to about one-quarter of a vibrational wavelength.

As another aspect of the invention, the dental scaler may include elongated casing means having a proximal end and a distal end, resilient support means within the casing means, a substantially rigid hollow shaft supported within the elongated casing means by the resilient support means, work tool connecting means attached to the distal end of the hollow shaft, the work tool connecting means capable of operatively connecting a work tool to the distal end of the hollow shaft, means for imparting vibration to the resiliently supported hollow shaft when the dental scaler is energized to provide vibratory movement to a work tool connected to the work tool connecting means, water transport means comprising a tube disposed substantially coaxially within the hollow shaft, support means for detachably supporting the water transport tube within the hollow shaft including sealing means disposed about the distal end of the tube for forming a water-tight seal between the hollow shaft and the water transport tube and flexible connecting means within the elongated casing means for detachably connecting the proximal end of the water transport tube to an external source of water.

As a part of either aspect of the invention, the hollow shaft can have shoulder means disposed upon an inner wall portion thereof, the shoulder means being disposed forwardly of the vibrational node, and the sealing means includes a cylindrically-shaped body in contact with the shoulder means and having a plurality of annular grooves each of which contains an O-ring such that water-tight seals are established with the adjacent surfaces of the hollow shaft and the water transport tube.

Dental scalers as described herein have an easily accessible and replaceable water transport tube which occupies a relatively small portion of the scaler housing. It is, therefore, quite compact affording good tactile control. Also, dental scalers of this invention have a water transport means which does not interfere with the vibratory pattern characteristic of this type of dental scaler. Inasmuch as only one water seal is necessary between the tube and its support within the hollow shaft, repair of the water transport means may be performed quickly and at relatively little expense.

DESCRIPTION OF PRESENTLY PREFERRED EMBODIMENTS

FIG. 1 is a perspective view of a dental scaling instrument of this invention;

FIG. 2 is a longitudinal side elevational view, partly in section, of the dental scaler of FIG. 1;

FIG. 3 is a perspective view of a water seal assembly suitable for sealing the water transport tube within the dental scalers of FIGS. 1 and 2;

FIG. 4 is a perspective view of the water transport tube shown in FIGS. 1 and 2;

FIG. 5 is a schematic representation of a typical standing wave generated by a dental scaler of this invention illustrating the position of vibratory nodes within the scaler body;

FIG. 6 is an enlarged fragmentary view of the water seal assembly which provides a water tight seal between the vibratory shaft and the water transport tube; and FIG. 7 is a side elevational view, partly in section, of the nose piece and work tool associated with the scaler of FIG. 1 showing the passageway and groove for directing water from the water transport tube to the end of the scaling tip.

Illustrated in FIG. 1 is a dental scaling instrument 10 comprising a handle 12 which includes a barrel 14 and a neck 16. Attached to the distal end 18 of scaler 10 is a nose piece 20. Secured within nose piece 20 is a shank 24 of a work tool or tip 26 having a curved end 28. As shown in detail in the cross-sectional view of FIG. 2, handle 12 provides an elongated casing within which is mounted resilient support means comprising a first or front resilient support 30 including a pair of O-rings 31. A second or rear resilient support is provided by a cylindrical tube 32 of resilient material which is sleevably engaged about a boss portion 34 secured to a rigid rear support 36. Disposed substantially coaxially with respect to elongated handle 12 is a vibratable, substantially rigid, hollow shaft 38. Nose piece 20 is connected to the distal end of hollow shaft 38.

Disposed about a mid-portion of shaft 38 is a sleeve-like rotor 40. As shown in FIG. 2, during operation of the scaler, rotor 40 is disposed substantially coaxially with respect to shaft 38, there being a gap 42 established between rotor 40 and an adjacent portion of side wall 44 of shaft 38. In an actual assembly with rotor 40 at rest, rotor 40 will be supported upon shaft 38 so that a portion of rotor 40 will rest upon side wall portions of shaft 38. Located in side wall portions of shaft 38 are a plurality of outlet ports 46 which connect passageway 48 of shaft 38 to gap 42.

As indicated by the arrows in FIG. 2, a fluid medium, such as compressed air, is supplied from a source (not shown) through a supply tube 49 which passes through an axially disposed opening 50 in end cap 51. The flow of compressed air passes into plenum 52 and through passageway 48 to fluid media outlet ports 46. The flow of compressed air which exhausts through outlet ports 46 strikes the inner wall rotor 40 and urges rotor 40 to rotate about the longitudinal axis of shaft 38. Each of outlet ports 46 has an axis which is offset or spaced at a distance from the longitudinal axis of shaft 38, such that each port axis does not intersect the axis of shaft 38. Thus each of ports 46 directs a jet of air at a glancing angle with respect to the inner wall of rotor 40 so as to impart rotary movement to rotor 40.

After imparting rotary movement to rotor 40, the air exhausts through the gap 42 between rotor 40 and shaft 38 and is then exhausted from the interior of barrel 14 through exhaust ports 56 disposed circumferentially about a rearward portion of barrel 14. Stop means comprising an annular-shaped guide 58 affixed to shaft 38 prevents travel of rotor 40 in an axial direction toward the forward or distal end of shaft 38. A further description of the manner in which the spinning rotor 40 imparts vibration to shaft 34 may be found in the aforementioned U.S. Pat. No. Re. 29,687, the disclosure of which is incorporated herein by reference.

The dental scaler further includes means for transporting water from an external source to work tool 26 and its curved end 28. A first water transport hose 100 located at the rearward or proximal end of scaler 10 is mounted in a detachable coupling 101. First water hose 100 is connected to an external source of water (not shown), the forward end of the hose being connected to one end of a rigid tube 103 which passes through a passageway in support body 102. Tube 103 is disposed substantially coaxially with respect to hollow shaft 38. Water transport tube 103 extends through hollow shaft 38 toward the distal end of scaler 10 and terminates distally from water seal assembly 110. Tube 103 is covered with an elastomeric tube covering 104 to eliminate vibration build-up within tube 103. The forward or distal end 106 of water tube 103 extends into plenum 108.

Water tube end 106 is supportably received within a water seal assembly 110 located at the forward or distal end of dental scaler 10. As shown in more detail in FIGS. 3 and 6, water seal assembly 110 comprises a cylindrical body 112 having a passageway 114 coaxially disposed with respect to the axis of body 112. Running circumferentially about the outer side wall of cylindrical body 112 are a pair of spaced annular grooves 116, one adjacent each end of cylindrical body 112. Disposed within each of grooves 116 is an O-ring 118 fabricated of a resilient material. O-rings 118 serve to position cylindrical body 112 within the forward end of hollow shaft 38 by frictional engagement of O-rings 118 with portions of inner wall 120 of hollow shaft 38. Within a mid-portion of cylindrical body 112 is a chamber formed by an annular groove 122 running circumferentially along a portion of inner wall 124 between grooves 116. Contained within groove 122 is an O-ring 126 which is in frictional engagement with the walls of groove 122 and with a portion of water tube end 105. O-ring 126 helps to properly position tube 104 centrally within hollow shaft 38.

Water seal assembly 110 provides a resilient support for water transport tube 103 within vibratable hollow shaft 38 by means of O-rings 118 and 126. Also, O-rings 118 and 126 provide a water-tight connection between plenum 108 and air passageway 48 within hollow shaft 38.

It is an advantage of the dental scaler of this invention that either, or both, of the water seal assembly 110 and water transport tube 103 are easily replaceable in the event of failure of one of the sealing O-rings or of clogging of the water tube. It is also a feature of this invention that a good water-tight seal is ensured by the sealing contact of the O-rings forming part of water seal assembly 110 with the adjacent portions of vibratable hollow shaft 38 and water tube 103. Illustrated in FIG. 5 is a schematic representation of a standing wave pattern generated within the dental scaler by vibration of shaft 38 at a frequency typically at about 6000 Hz. The standing wave characteristically has four vibrational nodes occurring at points "A", "B", "C" and "D". Node "A" occurs within or adjacent a portion of nose piece 20, node "B" within front suspension 30, node "C" at a mid-portion of vibratable hollow shaft 38 and node "D" close to rear suspension 32. Placement of the water seal assembly 110 close to a vibrational node (e.g., node "B") minimizes the amount of vibrational energy transferred to water tube 103 from hollow shaft 38, which transfer of vibration would drain energy from the vibrating shaft while at the same time cause turbulence within the water tube and/or possible vibratory failure of the tube.

It has been found that by positioning the center of gravity of water seal assembly 110 slightly forwardly of node "B", that is, toward the distal end of scaler 10, annular edge 130 of cylindrical body 112 is maintained in contact with a shoulder 132 in a wall portion of shaft 38. Provided water seal assembly 110 is so positioned with its center of gravity forward of node "B", the centrifugal conical whirl of shaft 38 during its vibratory movement imparts a force on cylindrical body 112 tending to move body 112 in a forward axial direction toward the distal end of scaler 10, which axial force ensures continuous contact between cylindrical body 112 and shoulder 132 without the need for supplemental retaining means. The magnitude of the axial force, $F_A$, acting on cylindrical body 112 may be calculated by the following equation $$F_A = mr\omega^2 \tan \alpha$$

wherein "m" is the mass of the water seal assembly, "r" is the radius of the orbit of revolution traced by the portion of the vibrating shaft for the particular axial position of the water seal assembly with respect to a node, "$\omega$" is the orbital speed of that portion of the vibratable shaft and "$\alpha$" is the angle established between the conically whirling vibratable shaft and the axis of the revolution of the shaft. This axial retaining force is especially needed to hold water seal assembly 110 in place when rotor 40 coasts to a standstill after the driving fluid is turned off, at which time there is no driving fluid pressure acting on assembly 110 to hold body 112 in its forwardmost distal position. The distance the water seal assembly should be positioned along the axis forward of node "B" can be related to the frequency of vibration, $\omega$. This distance forward of node "B" is up to about one-quarter of a vibrational wavelength, generally about one-sixteenth to about one-quarter of a vibrational wavelength, with the axial position of the center of gravity of the water seal assembly preferably being at a distance of just less than about one-quarter wavelength forward of the vibrational node.

During operation of the scaler when water seal assembly 110 is in contact with shoulder 132, plenum 108 receives water from tube 103 for delivery to a second or forward passageway 134 located at the distal end of the scaler. As can bests be seen in FIG. 7, second passageway 134 communicates with a further passageway 136 in the shank of nose piece 20 which, in turn, is in communication with a groove 138 in the surface of the work tool itself. The groove in the work tool provides a pathway for delivery of water along the working surfaces of work tool 26 to the scaling tip 28.

Although this invention has been described with reference to the incorporation of means for transporting water through the dental scaler of this invention, it is also contemplated that other fluids, such as medicaments (e.g., caries-removing liquids) or prophalytic or therapeutic agents (e.g., liquid fluoride compositions) compatible with dental practice can be used in conjunction therewith.

Although this invention has been described with reference to a dental scaler, it is also applicable to vibratory devices of like or similar configuration which are used for other purposes, such as medical, veterinary, and general industrial cleaning, polishing and deburring, etc. Such vibratory devices can have water, air, paraffin or other fluid materials transported therethrough in accordance with the teachings of this invention.

By centrally or axially positioning the water transport means of this invention within the vibratable hollow shaft, the overall size and dimension of the scaler does not change; therefore, good weight balance and tactile control are retained, and the scaler stays sufficiently small to be inserted, without undue comfort, into the patient's mouth. In addition, by supporting the water transport means and the vibratable shaft in the manner as shown, energy losses through transfer of vibration from the shaft to the water tube are minimized, as is generation of noise which might be objectionable to both operator and patient alike. Through use of the detachable coupling 101 and the water seal assembly 110, and the associated elements, as described herein, the water supply function is obtained in a manner which is readily repaired or replaced if the need arises.

While this invention has been described with reference to specific embodiments thereof, it should be understood by those skilled in this art that various changes may be made and equivalents may be substituted without departing from the true spirit and scope of the invention. In addition, various novel elements, as described herein, can be used individually or collectively, as desired. All such modifications are intended to be within the scope of the claims appended hereto.

What is claimed is:

1. A dental scaler comprising:
    elongated casing means having a proximal end and a distal end;
    resilient support means within said casing means;
    a substantially rigid hollow shaft supported within said elongated casing means by said resilient support means;
    work tool connecting means attached to the distal end of said hollow shaft, said work tool connecting means capable of operatively connecting a work tool to the distal end of said hollow shaft;

means for imparting vibration to said resiliently supported hollow shaft when said dental scaler is energized to provide vibratory movement to a work tool connected to said work tool connecting means;

water transport means comprising a tube disposed substantially coaxially within said hollow shaft, said tube having a proximal end and a distal end;

a water seal assembly for supporting the distal end of said water transport tube within said hollow shaft;

said dental scaler characterized by having a vibrational node near the distal end of said hollow shaft with said water seal assembly being disposed distally of the vibrational node and being retained in a sealing arrangement with said hollow shaft without supplemental retaining means.

2. The dental scaler of claim 1 wherein said hollow shaft has shoulder means disposed upon an inner wall portion of said hollow shaft, said shoulder means disposed distally of the vibrational node; and said water seal assembly comprises a hollow cylindrically-shaped body having a forward surface adapted to contact said hollow shaft shoulder means.

3. The dental scaler of claim 2 wherein said cylindrically-shaped body has a forward annular groove and a rearward annular groove on the exterior surface thereof, an O-ring disposed within said forward annular groove and an O-ring disposed within said rearward annular groove, said O-rings cooperating with portions of the inner wall of said hollow shaft to resiliently support said water seal assembly within said hollow shaft.

4. The dental scaler of claim 3 wherein one or both of said O-rings form a water-tight seal with said portions of the inner wall of said hollow shaft in contact therewith.

5. The dental scaler of claim 2 wherein said cylindrically-shaped body has a passageway extending therethrough, an annular groove in the wall of said cylindrically-shaped body defining said passageway, an O-ring within said groove for resiliently supporting said water transport tube within said passageway, said water transport tube forming a water-tight seal with said O-ring in contact therewith.

6. The dental scaler of claim 2 wherein said cylindrically-shaped body has a forward annular groove and a rearward annular groove on the exterior surface thereof, an O-ring disposed within each of said forward and rearward annular grooves, said O-rings cooperating with portions of the inner wall of said hollow shaft to resiliently support said water seal assembly within said hollow shaft; said cylindrically-shaped body has a passageway extending therethrough, an annular groove in the wall of said cylindrically-shaped body defining said passageway, said annular groove adjacent said passageway longitudinally positioned between said annular grooves on the exterior surface of said cylindrically-shaped body, an O-ring within said annular groove adjacent said passageway for resiliently supporting said water transport tube within said passageway, said water transport tube forming a water-tight seal with said O-ring in contact therewith.

7. The dental scaler of claim 1 further including means for removably mounting said water transport means within said hollow shaft.

8. The dental scaler of claim 7 wherein said mounting means includes said water seal assembly which supports the distal end of said water transport tube, and a detachable coupling positioning said proximal end of said water transport tube within the proximal end of said casing means.

9. The dental scaler of claim 8 wherein said coupling includes a support body having a passageway therethrough, the proximal end of said water transport tube passing through said passageway and adapted to be connected to an external source of water.

10. The dental scaler of claim 1 further including a water transport passageway extending through said work tool connecting means, the proximal end of said passageway being in operable connection with the distal end of said water transport tube.

11. The dental scaler of claim 10 further including a work tool operably connected to said work tool connecting means, said work tool having a groove extending longitudinally along the surface thereof, said groove being in communication with said passageway for transporting water from said water transport tube and said passageway to the distal end of said work tool.

12. The dental scaler of claim 1 wherein said water seal assembly is disposed distally of the vibrational node at a distance up to about one-quarter of a vibrational wavelength.

13. The dental scaler of claim 1 wherein said water seal assembly is disposed distally of the vibrational node at a distance of about one-sixteenth to about one-quarter of a vibrational wavelength.

14. A dental scaler comprising:

elongated casing means having a proximal end and a distal end;

resilient support means within said casing means;

a substantially rigid hollow shaft supported within said elongated casing means by said resilient support means;

work tool connecting means attached to the distal end of said hollow shaft, said work tool connecting means capable of operatively connecting a work tool to the distal end of said hollow shaft;

means for imparting vibration to said resiliently supported shaft when said dental scaler is energized by a gaseous fluid to provide the vibratory movement to a work tool connected to said work tool connecting means;

water transport means comprising a tube disposed substantially coaxially within said hollow shaft; and support means for detachably supporting said water transport tube within said hollow shaft, said support means comprising sealing means disposed about the distal end of said water transport tube for forming a water-tight seal between said hollow shaft and said water transport tube, and coupling means for positioning the proximal end of said water transport tube within the proximal end of said casing means.

15. The dental scaler of claim 14 wherein said coupling means includes a support body having a passageway therethrough, the proximal end of said water transport tube passing through said passageway and adapted to be connected to an external source of water.

16. The dental scaler of claim 14 wherein said hollow shaft has shoulder means disposed upon an inner wall portion adjacent the distal end thereof; and said sealing means comprises a hollow cylindrically-shaped body having a forward surface adapted to contact said hollow shaft shoulder means.

17. The dental scaler of claim 16 wherein said cylindrically-shaped body has a forward annular groove and a rearward annular groove on the exterior surface thereof, an O-ring disposed within said forward annular groove and an O-ring disposed within said rearward annular groove, said O-rings cooperating with portions of the inner walls of said hollow shaft to resiliently support said sealing means within said hollow shaft.

18. The dental scaler of claim 17 wherein one or both of said O-rings form a water-tight seal with said portions of the inner wall of said hollow shaft in contact therewith.

19. The dental scaler of claim 16 wherein said cylindrically-shaped body has a passageway extending therethrough, an annular groove in the wall of said cylindrically-shaped body defining said passageway, an O-ring within said groove for resiliently supporting said water transport tube within said passageway, said water transport tube forming a water-tight seal with said O-ring in contact therewith.

20. The dental scaler of claim 16 wherein said cylindrically-shaped body has a forward annular groove and a rearward annular groove on the exterior surface thereof, an O-ring disposed within each of said forward and rearward annular grooves, said O-rings cooperating with portions of the inner wall of said hollow shaft to resiliently support said cylindrically-shaped body within said hollow shaft; said cylindrically-shaped body has a passageway extending therethrough, an annular groove in the wall of said cylindrically-shaped body defining said passageway, said annular groove adjacent said passageway longitudinally positioned between said annular grooves on the exterior surface of said cylindrically-shaped body, an O-ring within said annular groove adjacent said passageway for resiliently supporting said water transport tube within said passageway, said water transport tube forming a water-tight seal with said O-ring in contact therewith.

21. The dental scaler of claim 14 further including a water transport passageway extending through said work tool connecting means, the proximal end of said passageway being in operable connection with the distal end of said water transport tube.

22. The dental scaler of claim 21 further including a work tool operably connected to said work tool connecting means, said work tool having a groove extending longitudinally along the surface thereof, said groove being in communication with said passageway for transporting water from said water transport tube and said passageway to the distal end of said work tool.

23. A vibratory device comprising:
elongated casing means having a proximal end and a distal end;
resilient support means within said casing means;
a substantially rigid hollow shaft supported within said elongated casing means by said resilient support means;
work tool connecting means attached to the distal end of said hollow shaft, said work tool connecting means capable of operatively connecting a work tool to the distal end of said hollow shaft;
means for imparting vibration to said resiliently supported hollow shaft when said vibratory device is energized to provide vibratory movement to a work tool connected to said work tool connecting means;
fluid transport means comprising a tube disposed substantially coaxially within said hollow shaft, said tube having a proximal end and a distal end;
a fluid seal assembly for supporting the distal end of said fluid transport tube within said hollow shaft;
said vibratory device characterized by having a vibrational node near the distal end of said hollow shaft with said fluid seal assembly being disposed distally of the vibrational node and being retained in a sealing arrangement with said hollow shaft without supplemental retaining means.

24. The vibratory device of claim 23 further including means for removably mounting said fluid transport means within said hollow shaft.

25. The vibratory device of claim 23 wherein said fluid seal assembly is disposed distally of the vibrational node at a distance up to about one-quarter of a vibrational wavelength.

26. A vibratory device comprising:
elongated casing means having a proximal end and a distal end;
resilient support means within said casing means;
a substantially rigid hollow shaft supported within said elongated casing means by said resilient support means;
work tool connecting means attached to the disftal end of said hollow shaft, said work tool connecting means capable of operatively connecting a work tool to the distal end of said hollow shaft;
means for imparting vibration to said resiliently supported shaft when said vibratory device is energized by a gaseous fluid to provide vibratory movement to a work tool connected to said work tool connecting means;
fluid transport means comprising a tube disposed substantially coaxially within said hollow shaft; and
support means for detachably supporting said fluid transport tube within said hollow shaft, said support means comprising sealing means disposed about the distal end of said fluid transport tube for forming a fluid-tight seal between said hollow shaft and said fluid transport tube, and coupling means for positioning the proximal end of said transport tube within the proximal end of said casing means.

27. The vibratory device of claim 26 wherein
said hollow shaft has shoulder means disposed upon an inner wall portion adjacent the distal end thereof; and
said sealing means comprises a hollow cylindrically-shaped body having a forward surface adapted to contact said hollow shaft should means.

28. The vibratory device of claim 27 wherein said cylindrically-shaped body has a forward annular groove and a rearward annular groove on the exterior surface thereof, an O-ring disposed within each of said forward and rearward annular grooves, said O-rings cooperating with portions of the inner wall of said hollow shaft to resiliently support said cylindrically-shaped body within said hollow shaft; said cylindrically-shaped body has a passageway extending therethrough, an annular groove in the wall of said cylindrically-shaped body defining said passageway, said annular groove adjacent said passageway longitudinally positioned between said annular grooves on the exterior surface of said cylindrically-shaped body, an O-ring within said annular groove adjacent said passageway for resiliently supporting said fluid transport tube within said passageway, said fluid transport tube forming a fluid-tight seal with said O-ring in contact therewith.

* * * * *